(12) United States Patent
Kikuchi et al.

(10) Patent No.: US 6,444,800 B1
(45) Date of Patent: Sep. 3, 2002

(54) HUMAN GASTRIC CANCER ANTIGEN GENE AND GASTRIC CANCER ANTIGEN PROTEIN

(75) Inventors: Kokichi Kikuchi, Sapporo (JP); Noriyuki Sato, Sapporo (JP); Toshihiko Torigoe, Sapporo (JP); Hiroeki Sahara, Sapporo (JP); Manabu Suzuki, Kawasaki (JP); Junji Hamuro, Kawasaaki (JP)

(73) Assignees: Ajinomoto Co., Inc., Tokyo (JP); Kokichi Kikuchi, Sapporo (JP)

( * ) Notice: Subject to any disclaimer, the term of this patent is extended or adjusted under 35 U.S.C. 154(b) by 0 days.

(21) Appl. No.: 09/348,265

(22) Filed: Jul. 7, 1999

(30) Foreign Application Priority Data

Jul. 13, 1998 (JP) .......................................... 10-197852

(51) Int. Cl.$^7$ .............................................. C07H 21/02
(52) U.S. Cl. ...................................... 536/23.1; 530/350
(58) Field of Search .......................... 536/23.1; 530/350

(56) References Cited

U.S. PATENT DOCUMENTS

| | | |
|---|---|---|
| 5,837,248 A | 11/1998 | Kikuchi et al. |
| 5,932,442 A * | 8/1999 | Lal et al. .................. 435/69.1 |
| 6,132,973 A | 10/2000 | Corley et al. |

FOREIGN PATENT DOCUMENTS

| | | |
|---|---|---|
| EP | 0 770 624 | 5/1997 |
| WO | WO 00/55350 | 9/2000 |

OTHER PUBLICATIONS

Yasoshima Takahiro et al: "The mechanism of the human autologous gastric signet ring cell tumor rejection by cytotoxic T lymphocytes in the possible context of HLA–A31 molecule." Cancer (Philadelphia), vol. 75, No. 6, Suppl, 1995, pp. 1484–1489, XP001015517 ISSN: 0008–543X.

Shu Qin Liu et al.: "Induction of Human Autologous Cytotoxic T Lymphocytes on Formalin–Fixed and Paraffin–Embedded Tumor Sections" Nature Medicine, vol. 1, No. 3, Mar. 1, 1995, pp. 267–271, XP002050775 ISSN; 1078–8956.

Sato Noriyuki et al: "Natural antigenic properties of gastric signet ring cell carcinomas." Gann Monograph on Cancer Research, vol. 48, 1999, pp. 31–41, XP001015519 ISBN: 3–8055–6980–7.

* cited by examiner

Primary Examiner—Sheela Huff
(74) Attorney, Agent, or Firm—Oblon, Spivak, McClelland, Maier & Neustadt, P.C.

(57) ABSTRACT

A tumor antigen gene is identified by screening a cDNA library derived from a gastric cancer cell line that can induce gastric cancer antigen specific cytotoxic T cell (CTL) by means of hybridization and PCR utilizing an amino acid sequence of peptide fragment of a known gastric cancer antigen protein, introducing a selected cDNA clone into a cell of gastric cancer cell line that cannot induce gastric cancer antigen specific CTL so that the clone should be expressed in the cell, and selecting a transgenic cell that has acquired the ability to induce CTL. According to the present invention, there are provided a protein capable of inducing immune response against human gastric cancer, DNA encoding the protein, as well as vaccine for treatment and prevention of human gastric cancer, and agent for treatment and prevention of human gastric cancer.

15 Claims, 1 Drawing Sheet

P.C.; positive control (HST-2)
N.C.; Negative control (PcDNAI)
c98 ; 0131cDNA-98

HUMAN GASTRIC CANCER ANTIGEN GENE AND GASTRIC CANCER ANTIGEN PROTEIN

TECHNICAL FIELD

The present invention relates to a protein capable of inducing a cytotoxic T cell (Cytotoxic T Lymphocytes, see "Ika Men'ekigaku (Medical Immunology), Revised 3rd Edition, Ed. by K. Kikuchi, also abbreviated as "CTL" hereinafter) against human gastric cancer cells in vivo or in vitro, and a DNA encoding the protein. Particularly, the present invention relates to a protein capable of presenting CTL against human gastric cancer cells by being bound to HLA-A31 antigen (Human Leucocyte Antigen, see "Gendai Men'ekigaku (Current Immunology)", 2nd Edition, Ed. By Y. Yamamura and T. Tada), and a DNA encoding the protein.

The present invention also relates to an agent for prevention or treatment of human gastric cancer, which comprises a protein capable of inducing CTL against human gastric cancer cells in vivo or in vitro, and a vaccine for prevention or treatment of human gastric cancer, which comprises a recombinant virus or a recombinant bacterium containing a DNA encoding the protein.

BACKGROUND ART

As the therapies for malignancy, in addition to surgical treatment, radiotherapy, and chemotherapy, there has been attempted immunotherapy which aims at obtaining therapeutic effect by enhancing the immune function of host patients. However, most of the immunotherapy procedures practically used thus far have obtained the effect by non-specifically enhancing immunecompetence of host patients, and drugs capable of inducing complete cure of tumors in clinical cases have not been practically used yet.

Many researchers have conducted investigations utilizing animal tumor models mainly based on mice to develop a drug capable of completely curing tumors. As a result, it has been clarified that tumors may be completely cured by efficiently inducing antigen specific immune responses, in particular, inducing cytotoxic T cells (CTLs), against tumor-associated antigens or tumor specific antigens expressed on various tumor cells. In order to treat tumors by such CTL induction, it is essential to elucidate an amino acid sequence of protein recognized by tumor specific CTL and a DNA sequence encoding the protein for each tumor.

In recent years, also for clinical tumors, it has been attempted to identify an antigen inducing tumor specific CTL and a DNA encoding the antigen, and utilize them for therapy.

Based on such conception, tumor antigen proteins capable of inducing CTL and DNAs encoding such proteins have been searched for. However, those identified so far are limited to the proteins such as those of MAGE family (T. Boon et al., *Immunology Today*, 18, 267–278, 1997), Mart-1, Thyrosinase, gp100 (S. A. Rosenberg, *Immunology Today*, 18, 175–182), which are the tumor antigens present in melanoma, and DNAs encoding them, and the proteins present in epidermoid cancer (derived from human head and neck cancer, CASP-8, *J. Exp. Med.*, 186, 785–793, 1997) and DNAs encoding them.

On the other hand, as for digestive tract cancers including gastric cancer, the presence of a tumor antigen peptide which can induce CTL has been identified by the present inventors (Japanese Patent Unexamined Publication [KOKAI] No. Hei 9-151200/1997). However, it has not been clarified at all what kind of protein from which tumor peptide is derived, and much less structure of DNA encoding the tumor antigen protein.

SUMMARY OF THE INVENTION

Accordingly, the object of the present invention is to provide 1) a DNA sequence encoding a protein which can induce immune response against human gastric cancer, 2) a protein sequence encoded by the aforementioned DNA, 3) a vaccine for treatment or prevention of human gastric cancer which comprises a recombinant virus or a recombinant bacterium containing the aforementioned DNA, and 4) an agent for treatment or prevention of human gastric cancer which comprises the aforementioned protein.

The present inventors noted that CTL recognizing tumor antigens played an important role as a biological defense mechanism against tumor cells. That is, the present inventors noted that efficient induction of CTL by utilizing a protein usable as a part of vaccine or a DNA encoding such a protein was effective for treatment and prevention of tumors, and conducted studies.

It has been known that the CTL induction against tumor antigens is achieved through specific expression of tumor antigen genes in tumor cells and presentation of antigenic peptides derived from the tumor antigen proteins on cell surfaces together with HLA antigens on tumor cells. Therefore, the present inventors attemped to identify a gene that is specifically expressed in a gastric cancer cell line capable of inducing CTL specific for gastric cancer cells.

As described above, the present inventors identified a tumor antigen peptide (also referred to as "F4.2 peptide" hereinafter) which can induce CTL against digestive tract cancers including gastric cancer, and elucidated its amino acid sequence (Japanese Patent Unexamined Publication [KOKAI] No. Hei 9-151200/1997). Therefore, they attempted to isolate a cDNA encoding a protein from which the peptide is derived from a cDNA library of gastric cancer cell line by hybridization technique utilizing that amino acid sequence. As a result, several hybridization positive cDNA clones were identified. From these clones, those that can be amplified by PCR utilizing primers corresponding to the sequence of F4.2 peptide were further selected. When nucleotide sequences of all provided clones were determined, however, any clone encoding a sequence containing an amino acid sequence exactly the same as F4.2 peptide was not found, while several clones containing partial sequences of F4.2 peptide were selected.

On the other hand, other than the hybridization technique mentioned above, the present inventors developed a method utilizing phenotypic alteration caused by gene transfer as an index as a method for identifying a tumor antigen gene capable of inducing CTL specific for a gastric cancer cell. That is, the present inventors conceived that a target tumor antigen gene could be identified by introducing a chromosome DNA fragment derived from a suitable cell line, or cDNA derived from gastric cancer cell line that can induce gastric cancer antigen specific CTL, into a cell line that cannot induce CTL so that the gene should be expressed in the cell, and selecting a transgenic clone that has acquired the ability to induce CTL.

The present inventors has already successfully established a CTL cell line (Tc-HST-2) derived from a gastric cancer patient, which specifically respond to tumor antigen restricted to HLA-A31, and a gastric cancer cell line (HST-2) derived from the same patient, which is recognized by the CTL cell line (*J. Immunol. Meth.*, 154; 235–243, 1992, Cancer, 75; 1484–1489, 1995). The gastric cancer cell line expresses HLA-A31 antigen. They have also succeeded in establishing a cell line (HOBC8-A31 cell) that expresses HLA-A31 antigen, but is not recognized by Tc-HST2 cells, and can be cultured in vitro. It is not expected that a gastric cancer antigen gene that can be expressed by HST-2 is expressed in that HOBC8-A31 cell.

When the aforementioned method utilizing phenotypic alteration as an index was applied to a cDNA clone encoding an amino acid sequence which contained a part of F4.2 peptide by using the aforementioned cell lines, it was found that a protein encoded by the cDNA activated the CTL cell line Tc-HST-2. Further, it was found that the cDNA was very useful as an agent for treatment and prevention of gastric cancer.

The present invention has been completed based on these findings.

That is, the present invention provides:

(1) A DNA which encodes a gastric cancer antigen protein present in a human gastric cancer cell (also referred to as the "DNA of the present invention" hereinafter).

(2) The DNA of above (1), which encodes a gastric cancer antigen protein which comprises an amino acid sequence of SEQ ID NO: 2.

(3) The DNA of above (1), which encodes a gastric cancer antigen protein which comprises an amino acid sequence of SEQ ID NO: 2 having substitution, deletion, insertion, addition or inversion of one or several amino acids, and which can activate a cytotoxic T cell recognizing a gastric cancer antigen protein.

(4) The DNA of above (2) which comprises at least nucleotides corresponding to the nucleotide numbers 46–534 of the nucleotide sequence of SEQ ID NO: 1.

(5) The DNA of above (2) which is hybridizable with a nucleotide sequence comprising at least nucleotides corresponding to the nucleotide numbers 46–534 of the nucleotide sequence of SEQ ID NO: 1 under a stringent condition, and which encodes a protein that can activate a cytotoxic T cell recognizing a gastric cancer antigen protein.

(6) The DNA of above (5), wherein the stringent condition is a condition in which washing is performed at 60° C., and at a salt concentration corresponding to 1×SSC and 0.1% SDS.

(7) The DNA of above (1), wherein the gastric cancer antigen protein encoded by the DNA comprises a partially modified amino acid sequence for realizing more efficient induction of a cytotoxic T cell recognizing the protein.

(8) A DNA which encodes a peptide containing an amino acid sequence comprising at least amino acids corresponding to amino acid numbers 62–70 of SEQ ID NO: 2, and being able to activate a cytotoxic T cell recognizing a gastric cancer antigen protein.

(9) A gastric cancer antigen protein which comprises an amino acid sequence of SEQ ID NO: 2.

(10) A gastric cancer antigen protein which comprises an amino acid sequence of SEQ ID NO: 2 having substitution, deletion, insertion, addition or inversion of one or several amino acids, and which can activate a cytotoxic T cell recognizing a gastric cancer antigen protein.

(11) A peptide which contains an amino acid sequence comprising at least amino acids corresponding to amino acid numbers 62–70 of SEQ ID NO: 2, and which can activate a cytotoxic T cell recognizing a gastric cancer antigen protein.

(12) A vaccine for prevention or treatment of human gastric cancer, which comprises a recombinant virus or a recombinant bacterium containing a DNA of any one of claims 1–8.

(13) An agent for prevention or treatment of human gastric cancer, which comprises the protein of above (9) or (10), or the peptide of above (11).

DETAILED DESCRIPTION OF THE INVENTION

Figure 1:
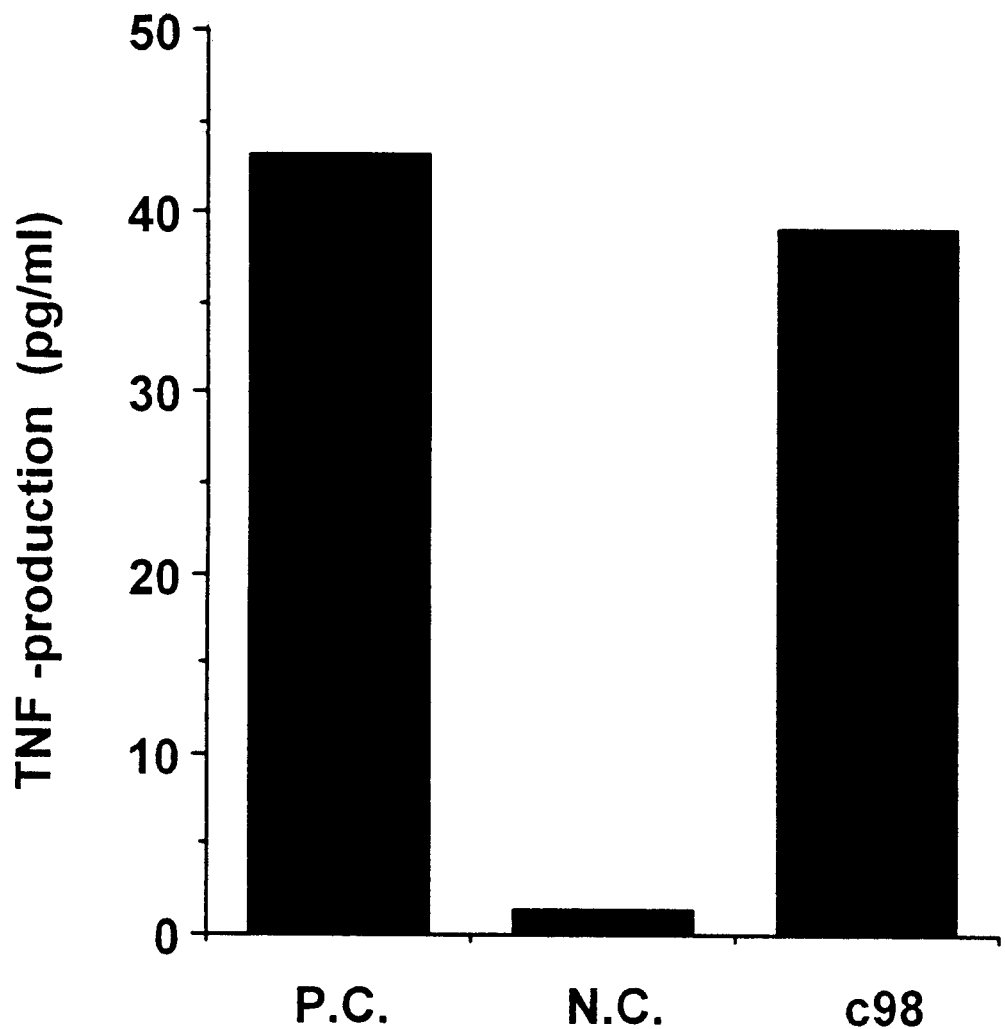
FIG. 1 shows a graph representing activity of HOBC8-A31 cells introduced with 0131cDNAc-98 for inducing CTL as to TC-HST-2.

The present invention will be explained in detail hereinafter.

The DNA of the present invention is a DNA encoding a gastric cancer antigen protein present in a human gastric cancer cell. The DNA encodes a protein that is expressed in a human gastric cancer cell, and can induce cytotoxic T cells targeting the gastric cancer cell when expressed in a cell expressing the same type HLA as that of the gastric cancer cell.

The method for obtaining the DNA of the present invention will be explained hereinafter. <1> Identification of cancer antigen gene that can induce gastric cancer cell specific CTL The DNA of the present invention can be identified by utilizing (1) a human gastric cancer cell line which can be cultured in vitro and of which HLA type has already been identified, (2) a CTL cell line which recognize the gastric cancer antigen which may be expressed by the foregoing gastric cancer cell line in the context of T cell receptor- and HLA-antigen-restriction, and can be cultured in a large scale in vitro, and (3) a cell line which expresses the same HLA as that of the aforementioned gastric cancer cell line, but does not express the gastric cancer gene, and can be cultured in a large scale in vitro. That is, the DNA of the present invention can be obtained by selection of the cDNA derived from the cell line (1) which is able to induce the CTL activity of the CTL cell line (2) when the cDNA is introduced into the cell line (3).

As the human gastric cancer cell line which can be cultured in vitro and of which HLA type has already been identified, for example, the HST-2 cell established by the present inventors can be used (J. Immunol. Meth., vol. 154, p 235–243 (1992); Jpn. J. Cancer Res., vol. 84, p 906–913 (1993)). This cell line is a gastric signet ring cell line established from cancerous ascites of a gastric cancer patient.

As the CTL cell line which exhibits cytotoxicity against the aforementioned cell line in the context of T cell receptor and HLA agntigen restriction, and can be cultured in a large scale in vitro, the Tc-HST-2 cell also established by present inventors can be used (J. Immunol. Meth., vol. 154, p 235–243 (1992); Jpn. J. Cancer Res., vol. 84, p 906–913 (1993)).

It is described in Cancer, vol.75, p1484–1489 (1995) that the aforementioned CTL cell specifically reacts with the HST-2 cell and that this CTL cell recognizes the HST-2 antigen (HST-2 cell specific antigen) in the context of HLA-A31 restriction.

As the cell line which expresses the same HLA antigen as that of the HST-2 gastric cancer cell line, more specifically the HLA-A31 antigen, which is utilized when the Tc-HST-2 cell recognizes the HST-2 cell, but does not express the gastric cancer gene, i.e., is not recognized by the Tc-HST2 cell, and can be cultured in vitro, the HOBC8-A31 cell established by the present inventors can be used.

In order to obtain a cDNA library comprising the gastric cancer antigen gene that can induce CTL activity of Tc-HST-2 cell, the HST-2 cell can be used. That is, the HST-2 cell can be cultured under a usual culture condition, for example, in RPMI1640 medium supplemented with fetal bovine serum, and washed with phosphate buffered saline (PBS), and mRNA can be purified from the cultured cells. Then, a cDNA library can be constructed from the mRNA by using a suitable vector. Techniques for mRNA purification, construction of cDNA library, gene transfer and the like are well known to those skilled in the art, and described in literature well known to those skilled in the art, for example, Sambrook, J., Fritsch, E. F., Maniatis, T., Molecular Cloning, Cold Spring Harbor Laboratory Press, 2nd edition and the like.

A cDNA clone of the gastric cancer antigen gene that can induce the CTL activity of the Tc-HST-2 cells can be identified by introducing the cDNAs of the aforementioned cDNA library into HOBC8-A31 cells, and examining if the transformed HOBC8-A31 cells can induce the CTL activity of Tc-HST-2 cells as a result of the gene transfer (CTL induction test).

If a transgenic HOBC8-A31 cell can induce the CTL activity or not can be determined by the chromic acid release test (Science, vol. 249, p 283–287 (1990)) or the TNF release test (*Immunogenetics*, vol. 35, p145 (1992)). In the TNF release test, transgenic cells are cultured at 37° C. for 48 hours, added with Tc-HST-2 cells, and further cultured for 12 hours, and TNF activity released in the culture supernatant is measured to detect the CTL induction activity.

The TNF activity can be measured by the method described in Immunogenetics, vol. 35, p145 (1992). That is, a TNF susceptive cell, for example, Wehi164 cells are mixed with a sample to be assayed (coculture of transformant cells and Tc-HST-2), cultured for 24 hours, then added with MTT (3-(4,5-dimethylthiazol-z-yl) 2,5-diphenyltetrazolium bromide) solution, and further cultured for 3 hours. Then, formazan produced by conversion from MTT in mitochondria of the Wehi164 cells is dissolved with acid propanol (e.g., propanol containing 0.01% hydrochloric acid), and its produced amount is determined by measuring absorbance ($OD_{570}$) to assay the TNF activity.

The method for identifying a cancer antigen gene which can induce the aforementioned gastric cancer cell specific CTL will be described in detail in the working examples hereinafter.

A DNA sequence of cDNA encoding a gastric cancer antigen gene capable of inducing the CTL activity of the Tc-HST-2 cell, which is identified as described above, can be determined in a conventional manner by using a DNA sequencer.

Specific examples of the DNA of the present invention include a DNA encoding a gastric cancer antigen protein having the amino acid sequence of SEQ ID NO: 2 depicted in SEQUENCE LISTING. More specific examples thereof include a DNA containing a nucleotide sequence comprising at least nucleotides corresponding to nucleotide numbers 46–534 of SEQ ID NO: 1 depicted in SEQUENCE LISTING. This DNA was identified by the aforementioned method as will be described in the examples hereinafter, and it is well understood by those skilled in the art that any codon encoding each amino acid residue in the amino acid sequence encoded by the DNA can be replaced with another equivalent codon.

The DNA of the present invention also include a DNA encoding a peptide having an amino acid sequence comprising at least amino acid residues corresponding to the amino acid numbers 62–70 of the amino acid sequence of SEQ ID NO: 2 depicted in SEQUENCE LISTING, more specifically, a DNA containing a sequence comprising, for example, nucleotides corresponding to the nucleotide numbers 229–255 of SEQ ID NO: 1. Such peptides also can induce the gastric cancer cell specific CTL like the protein of the present invention.

An *Escherichia coli* strain harboring a plasmid 0131cDNAc-98 containing a DNA having the nucleotide sequence shown in SEQ ID NO: 1 was given a private number AJ13489, and it was deposited at the National Institute of Bioscience and Human-Technology, Agency of Industrial Science and Technology, Ministry of International Trade and Industry (zip code 305–8566, 1-1-3 Higashi, Tsukuba-shi, Ibaraki-ken, Japan) on Jul. 10, 1998, as an accession number of FERM P-16895, and transferred from the original deposit to international deposit based on Budapest Treaty on Jun. 14, 1999, and has been deposited as deposit number of FERM BP-6759

Because the nucleotide sequence of the DNA having the nucleotide sequence shown in SEQ ID NO: 1 was elucidated by the present invention, such a DNA can be obtained by amplifying it from human chromosome DNA or a cDNA library derived from a gastric cancer cell line that can induce gastric cancer antigen specific CTL by PCR utilizing oligonucleotides produced based on that nucleotide sequence as primers, or by a conventional solid phase DNA synthesis technique. While the primers used for PCR are not particularly limited, oligonucleotides corresponding to regions upstream from the nucleotide number 46 and downstream from the nucleotide number 534 in the nucleotide sequence shown in SEQ ID NO: 1 are preferred.

The DNA of the present invention may be a gene derived from a chromosome, and may be interrupted with one or more introns so long as it encodes a gastric cancer antigen protein.

The DNA of the present invention may encode a gastric cancer antigen protein comprising substitution, deletion, insertion, addition or inversion of one or several amino acid residues at one or more sites so long as the activities of the encoded a gastric cancer antigen protein, i.e., the properties that it is recognized by cytotoxic T cells specific for the protein, and it can activate such cytotoxic T cells, are not deteriorated. The number meant by the term "several" herein used may vary depending on the positions in the higher order structures of the protein, kinds and the like of amino acid residues. This is arisen from the fact that there are highly analogous amino acids such as isoleucine and valine, and substitutions among such amino acids do not greatly affect the higher order structures of proteins.

A DNA encoding a protein substantially the same as the aforementioned gastric cancer antigen protein can be obtained by modifying the nucleotide sequence by, for example, site-specific mutagenesis so that the encoded amino acid sequence should have substitution, deletion, insertion, addition or inversion of amino acid residues at certain positions. Such a modified DNA as mentioned above can also be obtained by other conventional mutagenesis treatments. Examples of such treatments include, for example, a method involving in vitro treatment of DNA encoding a gastric cancer antigen protein with hydroxylamine or the like, method involving a treatment of a microorganism, e.g., a bacterium belonging to the genus Escherichia, harboring a DNA encoding a gastric cancer antigen protein with ultraviolet irradiation or an agent usually used for mutagenesis treatments such as N-methyl-N'-nitro-N-nitrosoguanidine (NTG) and nitrous acid.

A DNA encoding a protein substantially the same as the gastric cancer antigen protein can be obtained by expressing such a mutated DNA in suitable cells, and examining if it encodes a protein having the activities of the gastric cancer antigen protein using the aforementioned CTL induction test. A DNA encoding a protein substantially the same as the gastric cancer antigen protein can also be obtained by isolating a DNA that is hybridizable with a DNA having a nuclectide sequence comprising the nucleotides corresponding to the nucleotide numbers 46–534 of the nucleotide sequence of SEQ ID NO: 1 depicted in SEQUENCE LISTING or a part thereof under a stringent condition, and encodes a protein having activities of the gastric cancer antigen protein. The "stringent condition" herein used means a condition where a so-called specific hybrid is formed, but any non-specific hybrid is not formed. While it is difficult to numerically define the condition, exemplary conditions include one allowing hybridization of DNAs having a homology of 90% or more, but not allowing hybridization of DNAs having a homology less than 90%, and conditions under which DNA's are hybridized with each other at a salt concentration corresponding to an ordinary condition of washing in Southern hybridization, i.e., 60° C., 1×SSC, 0.1% SDS, preferably 0.1×SSC, 0.1% SDS.

While genes hybridizing under these conditions may contain those having been introduced with a stop codon, those having lost their activities and the like, they can be readily eliminated by the CTL induction test mentioned above.

Such modifications of the gastric cancer antigen protein as mentioned above may be one simply not impairing the activities of the gastric cancer antigen protein, but it is preferably one enabling more efficient induction of cytotoxic T cells recognizing the protein.

A gastric cancer antigen protein can be produced by ligating the DNA of the present invention to a suitable expression vector, transforming a cell such as BCG bacteria and bacteria belonging to the genus Escherichia with the vector, and culturing the resulting transformed cell. When a DNA having the nucleotide sequence shown in SEQ ID NO: 1 is used as the DNA of the present invention, a gastric cancer antigen protein having the amino acid sequence shown in SEQ ID NO: 2 can be obtained. When a modified DNA according to the present invention such as those mentioned above is used, a modified gastric cancer antigen protein can be obtained.

Because the DNA of the present invention, for example, a DNA having the DNA sequence of SEQ ID NO: 1 depicted in SEQUENCE LISTING or a part thereof, or a protein or peptide encoded by the DNA can induce gastric. cancer cell specific CTL, it is extremely hopeful as a therapeutic or prophylactic agent for human gastric cancer. For example, bacteria such as BCG bacteria that are transformed with a recombinant DNA obtained by introducing the DNA of the present invention into a suitable vector, and viruses such as vaccinia virus that carry the DNA of the present invention integrated into their genomes are effectively used as a live vaccine for treatment and prevention of human gastric cancer.

Dosage and administration may be similar to those used for conventional smallpox vaccination, BCG vaccine and the like.

When the protein or peptide of the present invention is used as a therapeutic or prophylactic agent for human gastric cancer, it can be administered 1) as it is, 2) together with a pharmaceutically acceptable carrier and/or diluent, or 3) by injection or transdermal absorption through spraying together with auxiliaries such as those mentioned below, if necessary. The carrier herein used include, for example, human serum albumin, and the diluent includes PBS, distilled water and the like.

BEST MODE FOR CARRYING OUT THE INVENTION

The present invention will be further explained in more detail with reference to the following examples, but the present invention is not limited to these examples.

EXAMPLE 1

Construction of cDNA Library From HST-2

HST-2 cells were cultured at 37° C. in RPMI1640 medium supplemented with fetal bovine serum. After $1 \times 10^8$ HST-2 cells were washed with phosphate buffered saline (PBS), the total RNA (1.9 mg) was extracted from the cells by using RNAgents Total RNA Isolation System (Promega company), and the mRNA (4 mg) was purified by using PolyATract system 1000 (Promega) The purification was performed by according to the protocol of Promega. cDNA (4 mg) was synthesized by using a cDNA synthesis kit (Amersham Pharmacia Biotech). The synthesized cDNA was ligated to BstX-1 adapter, and integrated into an expression vector, PcDNAI/Amp (Amersham Pharmacia Biotech). A cDNA library was constructed according to the protocol of Pmersham Pharmacia Biotech.

EXAMPLE 2

Screening for cDNA Encoding Peptide F4.2 by Hybridization

Cloning of cDNA by hybridization was performed by using GENE TRAPPER cDNA Positive Selection System (GIBCO). The procedure therefor will be outlined below. A degenerated primer encoding F4.2 (amino acid sequence is shown in SEQ ID NO: 3), F4.2×(5'-TAC TCY TGG ATG GAY AT-3': SEQ ID NO: 4), was synthesized and biotiylated. The cDNA library was digested at sense sequence side with the digestive enzymes contained in the aforementioned kit, GENE II protein and Exonuclease III, and thus made into single-stranded cDNA. The single-stranded cDNA was hybridized with the aforementioned biotiylated primer, and added with magnetic beads coated with streptavidin so that the cDNA hybridized to the biotiylated primer should be bound to the magnet beads through binding of biotin and streptavidin. Single-stranded cDNA was collected from the magnet beads, and restored into double-stranded cDNA using the above primer which was not biotiylated. This double-stranded cDNA was inserted into a vector pRC/RSV, and *Escherichia coli* was transformed with the obtained recombinant vector. In this manner, 3000 kinds of cDNA clones were obtained.

EXAMPLE 3

Screening for cDNA Clone Havina F4.2 Sequence by PCR

All of the cDNA clones provided in Example 2 were screened for a clone which contained a DNA sequence encoding F4.2 by PCR utilizing primers shown below.

As the forward primer for the PCR, various kinds of oligonucleotides having various kinds of sequences including a nucleotide sequence corresponding to the amino acid sequence of F4.2 (5'-TAC TCC TGG ATG GAC ATC-3', SEQ ID NO: 5). As the reverse primer, an oligonucleotide which had a sequence corresponding to a region located about 50 bp downstream from the insert of the vector (5'-TCT AGA TGC ATG CTC GAG-3', SEQ ID NO: 6) was used. The PCR was performed under the following conditions using a PCR apparatus (Thermal cycler, Applied Biosystem).

First step: 95° C. for 5 minutes

Second step: 95° C. for 30 seconds

Third step: 55° C. for 30 seconds

Fourth step: 72° C. for 30 seconds

Fifth step: 72° C. for 7 minutes

Among the above-mentioned steps, the second step to the fourth step were repeated for 30 times.

EXAMPLE 4

DNA Sequence Determination of cDNA Clone

Nucleotide sequences of the PCR products obtained in Example 3 were determined by using ABI PRISM 310 Genetic Analyzer (Applied Biosystem). The nucleotide sequence determination was performed according to the protocol of Applied Biosystem. No clone containing a sequence corresponding to the entire sequence of F4.2 was found among the clones whose sequences were determined. However, a clone having a sequence corresponding to a partial sequence of F4.2 was found among the clones whose sequences were determined (0131cDNAc-98). This close was obtained by using an oligonucleotide corresponding to the amino acid sequence shown in SEQ ID NO: 5 as the forward primer. The nucleotide sequence of this clone containing a sequence corresponding to a partial sequence of F4.2 is shown in SEQ ID NO: 1. The amino acid sequence that can be encoded by this sequence is shown in SEQ ID NO: 2.

EXAMPLE 5

Transformation of HOBC8-A31 Cell With 0131cDNAc-98 cDNA and Assay of Transformant Cell for Ability to Induce Activation of Tc-HST-2CTL Cell The cDNA obtained in Example 4 (0131cDNAc-98) was introduced into a cell line (HOBC8-A31) that did not express a gastric cancer gene to form transiently transformed cells. A gastric cancer patient-derived CTL cell line that specifically respond to a gastric cancer antigen in the context of HLA-A31 restriction was sensitized by the above transformant cell, and TNF produced by the responded CTL cell was added to a highly TNF-sensitive cell line. The ability of the transformant to induce activation of CTL cell was assayed by using the cytotoxic activity of TNF as an index.

The cDNA obtained in Example 4 (0131cDNAc-98) was introduced into HOBC8-A31 cells by using ripofectin. The transgenic cells were cultured at 37° C. in RPMI1640 medium supplemented with 0.1 ml of 10% FCS. After 48 hours, when transient gene expression was observed, $10^3$ of TcHST-2 cells (gastric cancer patient-derived CTL cell line that specifically responded to a gastric cancer antigen in the context of HLA-A31 restriction) were added to the cells, and co-cultured for 24 hours.

The cytotoxicity was assayed by the following MTT assay. That is, $7 \times 10^4$ cells of highly TNF-sensitive cell line Wehil64 (obtained from Ludwig Institute for Cancer Research, Brussels, Belgium) were suspended in a 120 μl volume, introduced into wells of a microtiter plate, each added with 30 μl of the culture supernatant from the aforementioned co-culture, and cultured for 24 hours. Then, 5 mg/ml solution of MTT (3-(4,5-dimethylthiazol-z-yl) 2,5-diphenyltetrazolium bromide) was added to each well, and then incubated for further three hours. Subsequently, 150 μl of propanol containing 0.01% hydrochloric acid was added to each well to solubilize formazon produced during the cultivation, and then TNF activity was determined by measuring absorbance at a wavelength of 570 nm.

The results are shown in FIG. 1. HST-2 cells were used as a positive control, and HOBCu-A31 cells transformed with a vector (PcDNAI) were used as a negative control. As seen from the results shown in FIG. 1, CTL induction activity for TC-HST-2 was confirmed in the HOBC8-A31 cells that were introduced with 0131cDNAc-98 (FIG. 1).

When a sequence of the nucleotide numbers 229–255 of the nucleotide sequence of SEQ ID NO: 1 depicted in SEQUENCE LISTING was introduced into cells and expressed in the same manner as described above, it was confirmed that the transformant cell line had the CTL induction activity for TC-HST-2.

---

What is claimed is:

1. A DNA which encodes a gastric cancer protein present in a human gastric signet ring cancer cell, wherein said protein comprises an amino acid sequence of SEQ ID NO:2.

2. The DNA according to claim 1, which comprises at least nucleotides corresponding to the nucleotide numbers 46–534 of the nucleotide sequence of SEQ ID NO: 1.

3. The DNA according to claim 1, which is hybridizable with a nucleotide sequence comprising at least nucleotides corresponding to the nucleotide numbers 46–534 of the nucleotide sequence of SEQ ID NO: 1 under a stringent condition, and which encodes a protein that can activate a cytotoxic T cell recognizing a gastric cancer antigen protein.

4. The DNA according to claim 3, wherein the stringent condition is a condition in which washing is performed at 60° C., and at a salt concentration corresponding to 1×SSC and 0.1% SDS.

5. A DNA which encodes a peptide consisting of amino acids 62–70 of SEQ ID NO:2, and being able to activate a cytotoxic T cell recognizing a gastric cancer antigen protein.

6. A vector comprising the DNA according to claim 1.
7. A vector comprising the DNA according to claim 2.
8. A vector comprising the DNA according to claim 3.
9. A vector comprising the DNA according to claim 4.
10. A vector comprising the DNA according to claim 5.
11. A host cell comprising the DNA according to claim 1.
12. A host cell comprising the DNA according to claim 2.
13. A host cell comprising the DNA according to claim 3.
14. A host cell comprising the DNA according to claim 4.
15. A host cell comprising the DNA according to claim 5.

* * * * *

SEQUENCE LISTING

<160> NUMBER OF SEQ ID NOS: 6

<210> SEQ ID NO 1
<211> LENGTH: 1093
<212> TYPE: DNA
<213> ORGANISM: Homo sapiens
<220> FEATURE:
<221> NAME/KEY: CDS
<222> LOCATION: (46)..(534)

<400> SEQUENCE: 1

```
cagtgtgctg ggaaaggttc gaacacggca cccgcactgc gcgtc atg gtg cag gcc      57
                                                 Met Val Gln Ala
                                                  1
```

```
tgg tat atg gga cga cgc ccc ggg cga ccc gcg gca acc cca ccg ccc      105
Trp Tyr Met Gly Arg Arg Pro Gly Arg Pro Ala Ala Thr Pro Pro Pro
 5              10                  15                  20 cga ccc cgg ccc gcc cag tgg ggc ctg gag cag ctg cgg cgg ctc ggg      153
Arg Pro Arg Pro Ala Gln Trp Gly Leu Glu Gln Leu Arg Arg Leu Gly
            25                  30                  35 gtg ctc tac tgg aag ctg gat gct gac aaa tat gag aat gat cca gaa      201
Val Leu Tyr Trp Lys Leu Asp Ala Asp Lys Tyr Glu Asn Asp Pro Glu
         40                  45                  50 tta gaa aag atc cga aga gag agg aac tac tcc tgg atg gac atc ata      249
Leu Glu Lys Ile Arg Arg Glu Arg Asn Tyr Ser Trp Met Asp Ile Ile
             55                  60                  65 acc ata tgc aaa gat aaa ctt cca aat tat gaa gaa aag att aag atg      297
Thr Ile Cys Lys Asp Lys Leu Pro Asn Tyr Glu Glu Lys Ile Lys Met
     70                  75                  80 ttc tac gag gag cat ttg cac ttg gac gat gag atc cgc tac atc ctg      345
Phe Tyr Glu Glu His Leu His Leu Asp Asp Glu Ile Arg Tyr Ile Leu
 85                  90                  95                 100 gat ggc agt ggg tac ttc gac gtg agg gac aag gag gac cag tgg atc      393
Asp Gly Ser Gly Tyr Phe Asp Val Arg Asp Lys Glu Asp Gln Trp Ile
                105                 110                 115 cgg atc ttc atg gag aag gga gac atg gtg acg ctc ccc gcg ggg atc      441
Arg Ile Phe Met Glu Lys Gly Asp Met Val Thr Leu Pro Ala Gly Ile
            120                 125                 130 tat cac cgc ttc acg gtg gac gag aag aac tac acg aag gcc atg cgg      489
Tyr His Arg Phe Thr Val Asp Glu Lys Asn Tyr Thr Lys Ala Met Arg
         135                 140                 145 ctt gtt tgt ggg aga acc ggt gtg gac agc gta caa ccg gcc cgc          534
Leu Val Cys Gly Arg Thr Gly Val Asp Ser Val Gln Pro Ala Arg
    150                 155                 160 tgaccatttt gaagcccgcg ggcagtaccg tgaaattctg gcacagaccg cctagcatgc     594
tgcctgggaa ctaacacgcg cctcgtaaag gtcccaatgt aatgacttga gcagaaaatc     654
aatactttct ctttgctttt agaggatagc taggttatct ttcctttgta agattatttg     714
atcagaatat tttgtaatga aaggatctag aaagcaactt ggaagtgtaa agagtcacct     774
tcattttctg taactcaatc aagactggtg ggtccatggc cctgtgttag ttcatgcatt     834
cagttgagtc ccaaatgaaa gtttcatctc ccgaaatgca gttccttaga tgcccatctg     894
gacgtgatgc cgcgcctgcc atgtaagaag gtgcaatcct agataacaca gctagccaga     954
tagaagacac ttttttctcc aaaatgatgc cttggggtgg ggagtggtag ggggaagagc    1014
tcccacccta aggggcacac actgagttgc ttatgccact tcttgttcaa ataaagtaa    1074 ctgccttaat cttactttc                                                1093

<210> SEQ ID NO 2
<211> LENGTH: 163
<212> TYPE: PRT
<213> ORGANISM: Homo sapiens

<400> SEQUENCE: 2

Met Val Gln Ala Trp Tyr Met Gly Arg Arg Pro Gly Arg Pro Ala Ala
 1               5                  10                  15

Thr Pro Pro Pro Arg Pro Arg Pro Ala Gln Trp Gly Leu Glu Gln Leu
                20                  25                  30

Arg Arg Leu Gly Val Leu Tyr Trp Lys Leu Asp Ala Asp Lys Tyr Glu
            35                  40                  45

Asn Asp Pro Glu Leu Glu Lys Ile Arg Arg Glu Arg Asn Tyr Ser Trp
         50                  55                  60
```

```
Met Asp Ile Ile Thr Ile Cys Lys Asp Lys Leu Pro Asn Tyr Glu Glu
 65                  70                  75                  80

Lys Ile Lys Met Phe Tyr Glu Glu His Leu His Leu Asp Asp Glu Ile
                 85                  90                  95

Arg Tyr Ile Leu Asp Gly Ser Gly Tyr Phe Asp Val Arg Asp Lys Glu
                100                 105                 110

Asp Gln Trp Ile Arg Ile Phe Met Glu Lys Gly Asp Met Val Thr Leu
            115                 120                 125

Pro Ala Gly Ile Tyr His Arg Phe Thr Val Asp Glu Lys Asn Tyr Thr
        130                 135                 140

Lys Ala Met Arg Leu Val Cys Gly Arg Thr Gly Val Asp Ser Val Gln
145                 150                 155                 160

Pro Ala Arg

<210> SEQ ID NO 3
<211> LENGTH: 10
<212> TYPE: PRT
<213> ORGANISM: Homo sapiens

<400> SEQUENCE: 3

Tyr Ser Trp Met Asp Ile Ser Cys Trp Ile
 1               5                   10

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 4
tactcytgga tggayat                                              17

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 5
tactcctgga tggacatc                                             18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:primer

<400> SEQUENCE: 6
tctagatgca tgctcgag                                             18
```